United States Patent
Su et al.

(10) Patent No.: US 12,403,215 B2
(45) Date of Patent: Sep. 2, 2025

(54) OXIDE LAYER-CONTAINING ZIRCONIUM-NIOBIUM ALLOY SHOULDER JOINT PROSTHESIS SYSTEM AND PREPARATION METHOD

(71) Applicant: Just Medical Devices (Tianjin) Co., Ltd., Tianjin (CN)

(72) Inventors: Bo Su, Tianjin (CN); Wen Shi, Tianjin (CN); Peng Zhang, Tianjin (CN); Zhenyu Huang, Tianjin (CN); Lu Liu, Tianjin (CN)

(73) Assignee: Just Medical Devices (Tianjin) Co., Ltd., Tianjin (CN)

( * ) Notice: Subject to any disclaimer, the term of this patent is extended or adjusted under 35 U.S.C. 154(b) by 374 days.

(21) Appl. No.: 17/910,210

(22) PCT Filed: Jun. 21, 2021

(86) PCT No.: PCT/CN2021/101290
§ 371 (c)(1),
(2) Date: Sep. 8, 2022

(87) PCT Pub. No.: WO2022/088706
PCT Pub. Date: May 5, 2022

(65) Prior Publication Data
US 2023/0248879 A1     Aug. 10, 2023

(30) Foreign Application Priority Data
Oct. 30, 2020   (CN) ......................... 202011200017.3

(51) Int. Cl.
*A61L 27/04*   (2006.01)
*A61F 2/30*    (2006.01)
(Continued)

(52) U.S. Cl.
CPC .......... *A61L 27/047* (2013.01); *A61F 2/4081* (2013.01); *A61L 27/56* (2013.01);
(Continued)

(58) Field of Classification Search
CPC .... A61L 27/047; A61L 27/56; A61L 2430/24; A61L 27/306; A61L 27/06; A61F 2/4081;
(Continued)

(56) References Cited

U.S. PATENT DOCUMENTS

| 5,509,933 A | 4/1996 | Davidson et al. |
| 2018/0029129 A1 | 2/2018 | Broadley et al. |
| 2018/0326493 A1* | 11/2018 | Gallagher ............... A61L 27/06 |

FOREIGN PATENT DOCUMENTS

| CN | 206424180 U | 8/2017 |
| CN | 107773330 A | 3/2018 |

(Continued)

OTHER PUBLICATIONS

International Search Report of PCT/CN2021/101290.
Written Opinion of PCT/CN2021/101290.

Primary Examiner — Ricardo D Morales (57) ABSTRACT

The present disclosure discloses a shoulder joint prosthesis containing zirconium-niobium alloy on oxidation layer and a preparation method thereof, the preparation method comprises: using zirconium-niobium alloy powder as a raw material, conducting a 3D printing for one-piece molding to obtain an intermediate products of the humeral handle with articular surface and the scapular glenoid plate, and performing Sinter-HIP, cryogenic cooling and surface oxidation to obtain humeral handle with articular surface and scapular glenoid plate. The prosthesis comprises a humeral handle, an articular surface, a humeral head and a scapular glenoid plate, a bone trabeculae is arranged on the outer surface of the upper part of the humeral handle, the upper surface of the (Continued)

scapular glenoid plate and the outer surface of the circular pipe with internal thread.

10 Claims, 9 Drawing Sheets

(51) Int. Cl.
| | | |
|---|---|---|
| A61F 2/40 | (2006.01) | |
| A61L 27/56 | (2006.01) | |
| B22F 10/64 | (2021.01) | |
| B22F 10/66 | (2021.01) | |
| B22F 10/68 | (2021.01) | |
| B33Y 10/00 | (2015.01) | |
| B33Y 40/20 | (2020.01) | |
| B33Y 80/00 | (2015.01) | |
| C22C 16/00 | (2006.01) | |
| C23C 8/12 | (2006.01) | |

(52) U.S. Cl.
CPC .............. *B22F 10/64* (2021.01); *B22F 10/66* (2021.01); *B22F 10/68* (2021.01); *B33Y 10/00* (2014.12); *B33Y 40/20* (2020.01); *B33Y 80/00* (2014.12); *C22C 16/00* (2013.01); *A61F 2002/30011* (2013.01); *A61F 2002/30224* (2013.01); *A61F 2002/30784* (2013.01); *A61F 2002/30822* (2013.01); *A61F 2002/30968* (2013.01); *A61F 2002/30985* (2013.01); *A61F 2002/4022* (2013.01); *A61F 2002/4033* (2013.01); *A61F 2310/00089* (2013.01); *A61F 2310/00095* (2013.01); *A61L 2430/24* (2013.01); *B22F 2201/11* (2013.01); *B22F 2201/12* (2013.01); *B22F 2301/205* (2013.01); *B22F 2998/10* (2013.01); *B22F 2999/00* (2013.01); *C23C 8/12* (2013.01)

(58) Field of Classification Search
CPC .. A61F 2002/30011; A61F 2002/30224; A61F 2002/30784; A61F 2002/30822; A61F 2002/30968; A61F 2002/30985; A61F 2002/4022; A61F 2002/4033; A61F 2310/00089; A61F 2310/00095; A61F 2002/30952; A61F 2/30767; A61F 2/4014; A61F 2/4059; A61F 2/3094; A61F 2002/30838; A61F 2002/3092; A61F 2002/3093; A61F 2002/30957; A61F 2002/4085; A61F 2002/3006; A61F 2002/30378; A61F 2002/30426; A61F 2002/3085; A61F 2002/30934; B22F 10/64; B22F 10/66; B22F 10/68; B22F 2201/11; B22F 2201/12; B22F 2301/205; B22F 2998/10; B22F 2999/00; B22F 3/15; B22F 10/28; B22F 3/00; B22F 3/24; B22F 7/08; B22F 2003/241; B22F 2003/248; B33Y 10/00; B33Y 40/20; B33Y 80/00; B33Y 70/00; C22C 16/00; C22C 1/0458; C23C 8/12; C23C 8/02; C23C 8/80; Y02P 10/25

See application file for complete search history.

(56) References Cited

FOREIGN PATENT DOCUMENTS

| CN | 108472730 A | 8/2018 |
|---|---|---|
| CN | 208838252 U | 5/2019 |
| CN | 111374805 A | 7/2020 |
| CN | 112294496 A | 2/2021 |

* cited by examiner

OXIDE LAYER-CONTAINING ZIRCONIUM-NIOBIUM ALLOY SHOULDER JOINT PROSTHESIS SYSTEM AND PREPARATION METHOD

CROSS-REFERENCE TO RELATED APPLICATIONS

This application is a national stage application of PCT/CN2021/101290. This application claims priorities from PCT Application No. PCT/CN2021/101290, filed Jun. 21, 2021, and from the Chinese patent application 202011200017.3 filed 10 Oct. 30, 2020, the content of which are incorporated herein in the entirety by reference.

TECHNICAL FIELD

The present disclosure relates to the technical field of artificial shoulder joint, in particular to the shoulder joint prosthesis containing zirconium-niobium alloy on oxidation layer and its preparation method.

BACKGROUND

Arthroplasty is one of the effective procedures for the treatment of end-stage diseases. However, after the joint prosthesis has been implanted into the human body for a long time, soft materials, such as ultra-high molecular weight polyethylene (UHMWPE), will produce a large number of wear debris particles due to the wear of the articular surface under the long-term action of the complex physiological and mechanical environment in the body. The accumulation of wear debris can cause a series of tissue reactions, leading to osteolysis, aseptic loosening and prosthesis failure. Moreover, metal joint materials such as cobalt chromium alloy, nickel titanium alloy and stainless steel alloy will release toxic metal ions under the long-term joint action of internal friction and corrosion, such as Cr, Ni, Mn, Mo and V ions, which will cause allergic reaction and other unknown potential hazards.

Zirconium-niobium alloy has been gradually used in the field of medical devices for its excellent corrosion resistance, mechanical properties and good biocompatibility. Zirconium-niobium alloy can react with N, C, O or other elements to form a hard oxidation layer on the surface. It has excellent wear resistance and low wear rate, which can reduce the wear of soft materials, that is, it has excellent wear resistance of joint articular surface. Moreover, the oxidation layer can reduce the release of metal ions and has excellent biocompatibility, that is, excellent biocompatibility at the osseointegration interface. The low wear rate of the articular surface is combined organically with the osseointegration interface (trabeculae), which has excellent bone ingrowth performance, enabling the prosthesis to achieve the advantages of both interfaces at the same time.

Currently, the artificial prostheses used in clinical practice include bone cement fixation prosthesis and cementless fixation prosthesis. Studies have shown that the high temperature generated by the cemented prosthesis during the solidification of bone cement will cause the death of some bone cells so as to affect the bone growth. Cementless fixation prosthesis has been widely used due to its good bone growth performance. The osseointegration interface of cementless prosthesis is usually sprayed with hydroxyapatite coating or titanium coating, which has the advantage of overcoming the high temperature during the solidification of bone cement conductive to the growth of bone cells, and the disadvantage is that the surface coating is easy to fall off, which affects the use effect and will cause surgical failure in extreme cases. With the development of 3D printing technology, porous metal bone trabeculae made of 3D printing technology provided on the surface of prosthesis in contact with host bone tissue can solve the problem of coating falling off, and also can realize bone ingrowth instead of bone growth. However, the solid part of the 3D printing products have the problems such as uneven microstructure and internal defects, resulting in poor mechanical properties. The failure of powder fusion in part of trabecular structure also results in poor mechanical properties.

Therefore, it is of great significance to fabricate a shoulder joint prosthesis containing zirconium-niobium alloy on oxidation layer with excellent mechanical properties and realize the advantages of two interfaces.

SUMMARY

One of the objectives of the present disclosure is to overcome the deficiencies of the existing technology to provide a shoulder joint prosthesis containing zirconium-niobium alloy on oxidation layer.

The second purpose of the present disclosure is to provide a preparation method of the shoulder joint prosthesis containing zirconium-niobium alloy on oxidation layer.

The technical scheme of the present disclosure is summarized as follows:

The preparation method of shoulder joint prosthesis containing zirconium-niobium alloy on oxidation layer includes the following steps:

1) Preparation of Humeral Handle with One Articular Surface or Scapular Glenoid Plate 1-1) Using zirconium-niobium alloy powder as the raw material, conducting a 3D printing for one-piece molding, and obtaining a first intermediate of the humeral handle with an articular surface and a first intermediate of the scapular glenoid plate, putting the two first intermediates into the Sinter-HIP furnace, heating to 1250° C.-1400° C. under helium/argon gas protection, placing at a constant pressure of 140 MPa-180 MPa for 1 h to 3 h, reducing to a normal pressure, cooling to below 200° C. with the furnace, taking them out, and obtaining a second intermediate of the humeral handle and a second intermediate of the scapular glenoid plate;

1-2) Placing two second intermediate products in a programmable thermostat to cool to −80° C. to −120° C. at a rate of 1° C./min, keeping them at a constant temperature for 5 h to 10 h, and taking them out of the programmed thermostat; placing them in a liquid nitrogen for 16 h to 36 h, and adjusting the temperature to a room temperature so as to obtain a third intermediate of the humeral handle and a third intermediate of the scapular glenoid plate;

1-3) Placing two third intermediate products in a programmable thermostat to cool to −80° C. to −120° C. at a rate of 1° C./min, and placing them at a constant temperature for 5 h to 10 h, taking them out of the programmed thermostat, placing them in the liquid nitrogen for 16 h to 36 h and adjusting the temperature to room temperature so as to obtain a fourth intermediate of the humeral handle and a fourth intermediate of the scapular glenoid plate;

1-4) Machining, finishing, polishing, cleaning, and drying the fourth intermediate products, and obtaining a fifth intermediate of the humeral handle and a fifth intermediate of the scapular glenoid plate; the roughness of the hemispherical groove of the fifth intermediate product of the humeral handle is Ra≤0.050 μm;

1-5) Placing the two fifth intermediate products in a tube furnace, introducing normal-pressure helium/argon gas containing 5% to 15% of oxygen in percentage by mass, heating to 500° C. to 700° C. at 5° C./min to 20° C./min, and cooling down to 400° C. to 495° C. at 0.4° C./min to 0.9° C./min; and cooling to be below 200° C. sequentially, taking them out to obtain the humeral handle with one articular surface and the scapular glenoid plate.

The structure of the humeral handle with an articular surface is the same as its first intermediate, second intermediate, third intermediate, fourth intermediate, and fifth intermediate.

The structure of the scapular glenoid plate is the same as its first intermediate, second intermediate, third intermediate, fourth intermediate, and fifth intermediate.

2) Preparation of Humeral Head 2-1) Machining, finishing, polishing, cleaning, and drying forged pieces containing zirconium-niobium alloy to obtain the intermediate product of the humeral head; the roughness of the outer surface of the intermediate products of the humeral head is Ra≤0.050 μm;

2-2) placing the intermediate product of the humeral head in a tubular furnace, introducing normal-pressure helium/argon gas containing 5% to 15% of oxygen in percentage by mass, heating to 500° C. to 700° C. at 5° C./min to 20° C./min, and cooling to 400° C. to 495° C. at 0.4° C./min to 0.9° C./min; and natural cooling to be below 200° C. sequentially, taking them out to obtain the humeral head.

The shoulder joint prosthesis containing zirconium-niobium alloy on oxidation layer comprises the humeral handle 1, the articular surface 12, the humeral head 2 and the scapular glenoid plate 3, the upper end of the articular surface 12 is provided with a hemispherical groove 13, the humeral head 2 is connected with the hemispherical groove 13 in a sliding mode, and the humeral head 2 is buckle-connected with the scapular glenoid plate 3; the scapular glenoid plate 3 is fixedly connected with a circular pipe 33 with internal thread and a hole 31 with internal thread, and the humeral handle 1 and the articular surface 12 are fixedly connected into a humeral handle with articular surface; a bone trabeculae 4 is arranged on the outer surface of the upper part of the humeral handle 1, the upper surface of the scapular glenoid plate 3 and the outer surface of the circular pipe 33.

The chemical composition of the zirconium-niobium alloy powder in percentage by mass is respectively 85.6%-96.5% of Zr, 1.0%-12.5% of Nb, and the rest are unavoidable impurities; where a particle size of the zirconium-niobium alloy powder ranges from 45 to 150 μm.

The chemical composition of the forged pieces containing zirconium-niobium alloy powder in percentage by mass is respectively 85.6%-96.5% of Zr, 1.0%-12.5% of Nb, and the rest are unavoidable impurities.

The specific steps for adjusting the temperature in steps 1-2) and 1-3) are: increasing the temperature to −120° C. to −80° C. and keeping the constant temperature for 3 h to 5 h; then increasing the temperature to −40° C. to −20° C. and keeping the constant temperature for 3 h to 5 h and then increasing the temperature to 4° C. to 8° C. and keeping the constant temperature for 1 h to 3 h and then increasing the temperature.

The pore size of the bone trabeculae 4 ranges from 0.35 mm to 1.10 mm, the porosity ranges from 55% to 78%, through-hole ratio is 100%.

The shoulder joint prosthesis containing zirconium-niobium alloy on oxidation layer prepared by the above method.

Compared with the existing technical solutions, the present disclosure has the following beneficial effects:

The bone trabeculae of the present disclosure is arranged at the outer surface of the upper part of the humeral handle, the upper surface of the scapular glenoid plate and the outer surface of the circular pipe so as to improve the bone ingrowth. The humeral handle with articular surface and the scapular glenoid plate of the present disclosure are integrated with 3D printing, which solves the problem that the complex structure cannot be prepared by traditional machining; and has high bonding strength between trabeculae and the matrix, therefore it is not easy to fall off, thereby improving the service life of the prosthesis. The integral shoulder joint prosthesis containing zirconium-niobium alloy on oxidation layer of the present disclosure realizes the excellent biocompatibility of bone integration interface, bone ingrowth ability, super wear resistance and low wear rate of friction interface. There is an oxygen-rich layer between the oxidation layers of the humeral handle, humeral head and scapular glenoid plate and the matrix, which acts as a transition layer to improve adhesion between the oxidation layer and the matrix, and prevent the oxidation layer from falling off, and the oxidation layer has high hardness. The shoulder joint prosthesis according to the present disclosure has low artifact, little interference to nuclear magnetic field and can be used for nuclear magnetic detection. The humeral handle and its articular surface are fixed connected and integrated so as to reduce fretting.

DETAILED DESCRIPTION OF THE EMBODIMENTS

The present disclosure will be further described below with the drawings and embodiments.

Embodiment 1

The preparation method of the shoulder joint prosthesis containing zirconium-niobium alloy on oxidation layer includes the following steps:

The preparation method of shoulder joint prosthesis containing zirconium-niobium alloy on oxidation layer includes the following steps:

1) Preparation of Humeral Handle with One Articular Surface or Scapular Glenoid Plate 1-1) Using zirconium-niobium alloy powder as the raw material, conducting a 3D printing for one-piece molding, and obtaining a first intermediate of the humeral handle with an articular surface and a first intermediate of the scapular glenoid plate, putting the two first intermediates (e.g. the first intermediate of the humeral handle with an articular surface and the first intermediate of the scapular glenoid plate) into the Sinter-HIP furnace, heating to 1250° C. under argon gas protection, placing at a constant pressure of 180 MPa for 3 h, reducing to a normal pressure, cooling to below 200° C. with the furnace, taking them out, and obtaining a second intermediate of the humeral handle and a second intermediate of the scapular glenoid plate;

1-2) Placing two second intermediate products in a programmable thermostat to cool to −80° C. at a rate of 1° C./min, keeping them at a constant temperature for 10 h, and taking them out of the programmed thermostat; placing them in a liquid nitrogen for 16 h, and adjusting the temperature to a room temperature so as to obtain a third intermediate of the humeral handle and a third intermediate of the scapular glenoid plate;

1-3) Placing two third intermediate products in a programmable thermostat to cool to −80° C. at a rate of 1° C./min, and placing them at a constant temperature for 10 h, taking them out of the programmed thermostat, placing them in the liquid nitrogen for 16 h and adjusting the temperature to room temperature so as to obtain a fourth intermediate of the humeral handle and a fourth intermediate of the scapular glenoid plate;

1-4) Machining, finishing, polishing, cleaning, and drying the fourth intermediate products, and obtaining a fifth intermediate of the humeral handle and a fifth intermediate of the scapular glenoid plate; the roughness of the hemispherical groove 13 of the fifth intermediate product of the humeral handle is Ra=0.012 μm;

1-5) Placing the two fifth intermediate products in a tube furnace, introducing normal-pressure argon gas containing 5% of oxygen in percentage by mass, heating to 500° C. at 5° C./min, and cooling down to 400° C. at 0.4° C./min; and cooling to be below 200° C. sequentially, taking them out to obtain the humeral handle with the articular surface and the scapular glenoid plate.

The structure of the humeral handle with one articular surface is the same as its first intermediate, second intermediate, third intermediate, fourth intermediate, and fifth intermediate.

The structure of the scapular glenoid plate is the same as its first intermediate, second intermediate, third intermediate, fourth intermediate, and fifth intermediate.

2) Preparation of Humeral Head 2-1) Machining, finishing, polishing, cleaning, and drying forged pieces containing zirconium-niobium alloy to obtain the intermediate product of the humeral head; the roughness of the outer surface of the intermediate products of the humeral head is Ra=0.012 μm;

2-2) placing the intermediate product of the humeral head in a tubular furnace, introducing normal-pressure argon gas containing 5% of oxygen in percentage by mass, heating to 500° C. at 5° C./min, and cooling to 400° C. at 0.4° C./min; and natural cooling to be below 200° C. sequentially, taking them out to obtain the humeral head.

Figure 1:
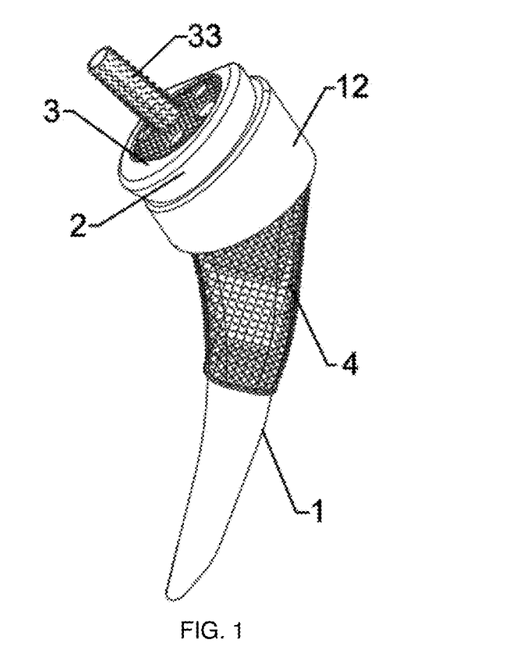
FIG. 1 is a schematic diagram of shoulder joint prosthesis containing zirconium-niobium alloy on oxidation layer of the present disclosure.
Figure 2:
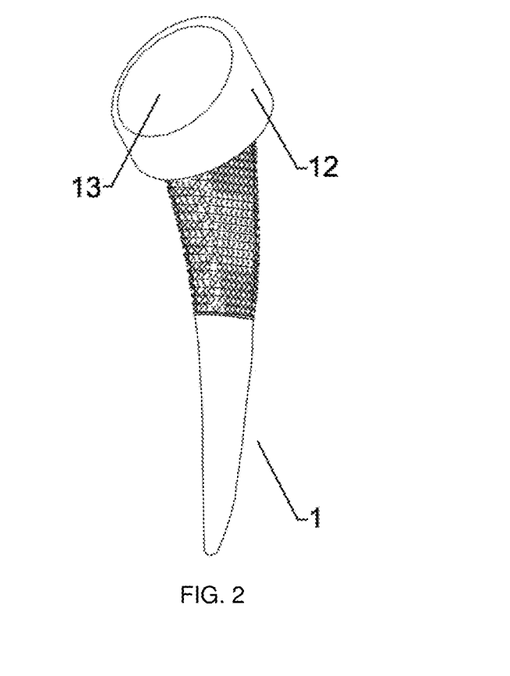
FIG. 2 is an axonometric diagram of humeral handle with articular surface.
Figure 3:
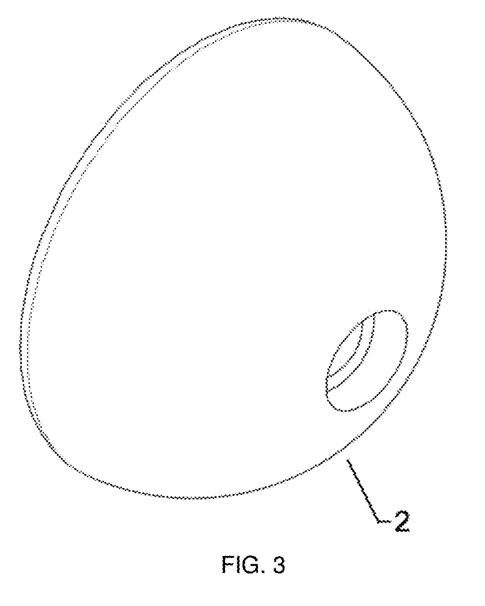
FIG. 3 is an axonometric diagram of humeral head observed from the outer surface.
Figure 4:
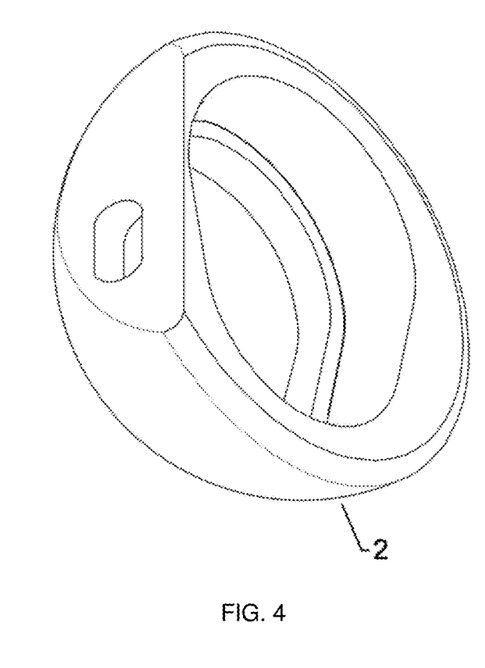
FIG. 4 is an axonometric diagram of humeral head observed from the inner surface.
Figure 5:
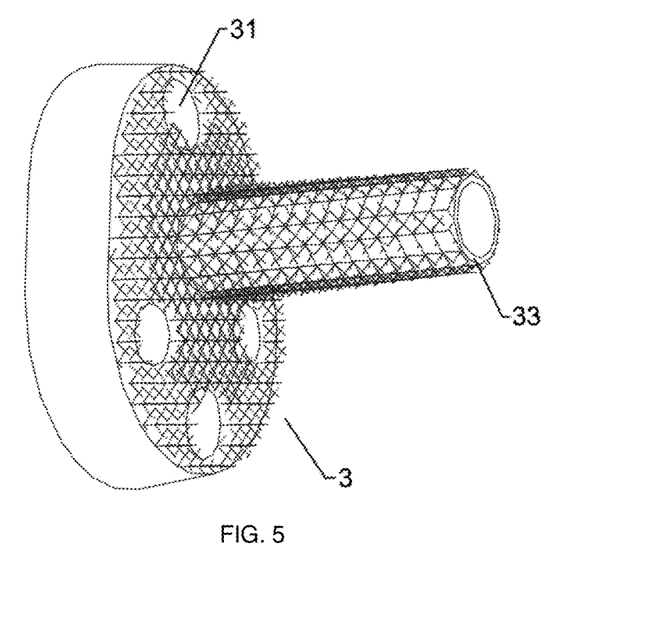
FIG. 5 is an axonometric diagram of scapular glenoid plate.

As shown in FIG. 1, the shoulder joint prosthesis containing zirconium-niobium alloy on oxidation layer comprises a humeral handle 1, an articular surface 12, a humeral head 2 and a scapular glenoid plate 3, the upper end of the articular surface 12 is provided with a hemispherical groove 13, the humeral head 2 is connected with the hemispherical groove 13 in a sliding mode, and the humeral head 2 is buckle-connected with the scapular glenoid plate 3; the scapular glenoid plate 3 is fixedly connected with a circular pipe 33 with internal thread and a hole 31 with internal thread, and the humeral handle 1 and the articular surface 12 are fixedly connected into a humeral handle with articular surface, as shown in FIG. 2; a bone trabeculae 4 is arranged on the outer surface of the upper part of the humeral handle 1, the upper surface of the scapular glenoid plate 3 and the outer surface of the circular pipe 33.

The chemical composition of the zirconium-niobium alloy powder in percentage by mass is respectively 85.6% of Zr, 12.5% of Nb, and the rest are unavoidable impurities; where a particle size of the zirconium-niobium alloy powder ranges from to 150 μm, purchased from Xi'an Sailong Metal Material Co., Ltd.

The chemical composition of the forged pieces containing zirconium-niobium alloy powder in percentage by mass is respectively 85.6% of Zr, 12.5% of Nb, and the rest are unavoidable impurities, purchased from Xi'an Sailong Metal Material Co., Ltd.

The specific steps for adjusting the temperature in steps 1-2) and 1-3) are: increasing the temperature to −120° C. and keeping the constant temperature for 5 h; then increasing the temperature to −40° C. and keeping the constant temperature for 5 h and then increasing the temperature to 4° C. and keeping the constant temperature for 3 h and then increasing the temperature.

The pore size of the bone trabeculae 4 is 0.80 mm, the porosity is 72%, through-hole ratio is 100%.

Embodiment 2

The preparation method of the shoulder joint prosthesis containing zirconium-niobium alloy on oxidation layer includes the following steps:

The preparation method of shoulder joint prosthesis containing zirconium-niobium alloy on oxidation layer includes the following steps:

1) Preparation of Humeral Handle with One Articular Surface or Scapular Glenoid Plate 1-1) Using zirconium-niobium alloy powder as the raw material, conducting a 3D printing for one-piece molding, and obtaining a first intermediate of the humeral handle with an articular surface and a first intermediate of the scapular glenoid plate, putting the two first intermediates into the Sinter-HIP furnace, heating to 1325° C. under helium gas protection, placing at a constant pressure of 160 MPa for 2 h, reducing to a normal pressure, cooling to below 200° C. with the furnace, taking them out, and obtaining a second intermediate of the humeral handle and a second intermediate of the scapular glenoid plate;

1-2) Placing two second intermediate products in a programmable thermostat to cool to −100° C. at a rate of 1° C./min, keeping them at a constant temperature for 7 h, and taking them out of the programmed thermostat; placing them in a liquid nitrogen for 24 h, and adjusting the temperature to a room temperature so as to obtain a third intermediate of the humeral handle and a third intermediate of the scapular glenoid plate;

1-3) Placing two third intermediate products in a programmable thermostat to cool to −100° C. at a rate of 1° C./min, and placing them at a constant temperature for 7 h, taking them out of the programmed thermostat, placing them in the liquid nitrogen for 24 h and adjusting the temperature to room temperature so as to obtain a fourth intermediate of the humeral handle and a fourth intermediate of the scapular glenoid plate;

1-4) Machining, finishing, polishing, cleaning, and drying the fourth intermediate products, and obtaining a fifth intermediate of the humeral handle and a fifth intermediate of the scapular glenoid plate; the roughness of the hemispherical groove of the fifth intermediate product of the humeral handle is Ra=0.035 μm;

1-5) Placing the two fifth intermediate products in a tube furnace, introducing normal-pressure helium gas containing 10% of oxygen in percentage by mass, heating to 600° C. at 15° C./min, and cooling down to 450° C. at 0.7° C./min; and cooling to be below 200° C. sequentially, taking them out to obtain the humeral handle with one articular surface and the scapular glenoid plate.

The structure of the humeral handle with an articular surface is the same as its first intermediate, second intermediate, third intermediate, fourth intermediate, and fifth intermediate.

The structure of the scapular glenoid plate is the same as its first intermediate, second intermediate, third intermediate, fourth intermediate, and fifth intermediate.

2) Preparation of Humeral Head 2-1) Machining, finishing, polishing, cleaning, and drying forged pieces containing zirconium-niobium alloy to obtain the intermediate product of the humeral head; the roughness of the outer surface of the intermediate products of the humeral head is Ra=0.035 μm;

2-2) placing the intermediate product of the humeral head in a tubular furnace, introducing normal-pressure helium gas containing 10% of oxygen in percentage by mass, heating to 600° C. at 15° C./min, and cooling to 450° C. at 0.7° C./min; and natural cooling to be below 200° C. sequentially, taking them out to obtain the humeral head.

The shoulder joint prosthesis containing zirconium-niobium alloy on oxidation layer comprises a humeral handle 1, an articular surface 12, a humeral head 2 and a scapular glenoid plate 3, the upper end of the articular surface 12 is provided with a hemispherical groove 13, the humeral head 2 is connected with the hemispherical groove 13 in a sliding mode, and the humeral head 2 is buckle-connected with the scapular glenoid plate 3; the scapular glenoid plate 3 is fixedly connected with a circular pipe 33 with internal thread and a hole 31 with internal thread, and the humeral handle 1 and the articular surface 12 are fixedly connected into a humeral handle with articular surface; a bone trabeculae 4 is arranged on the outer surface of the upper part of the humeral handle 1, the upper surface of the scapular glenoid plate 3 and the outer surface of the circular pipe 33.

The chemical composition of the zirconium-niobium alloy powder in percentage by mass is respectively 93.4% of Zr, 5.1% of Nb, and the rest are unavoidable impurities; where a particle size of the zirconium-niobium alloy powder ranges from 45 to 150 μm, which is purchased from Xi'an Sailong Metal Material Co., Ltd.

The chemical composition of the forged pieces containing zirconium-niobium alloy powder in percentage by mass is respectively 93.4% of Zr, 5.1% of Nb, and the rest are unavoidable impurities, which is purchased from Xi'an Sailong Metal Material Co., Ltd.

The specific steps for adjusting the temperature in steps 1-2) and 1-3) are: increasing the temperature to −100° C. and keeping the constant temperature for 4 h; then increasing the temperature to −30° C. and keeping the constant temperature for 4 h and then increasing the temperature to 6° C. and keeping the constant temperature for 2 h and then increasing the temperature.

The pore size of the bone trabeculae 4 is 0.35 mm, the porosity is 55%, through-hole ratio is 100%.

Embodiment 3

The preparation method of the shoulder joint prosthesis containing zirconium-niobium alloy on oxidation layer includes the following steps: The preparation method of shoulder joint prosthesis containing zirconium-niobium alloy on oxidation layer includes the following steps:

1) Preparation of Humeral Handle with One Articular Surface or Scapular Glenoid Plate 1-1) Using zirconium-niobium alloy powder as the raw material, conducting a 3D printing for one-piece molding, and obtaining a first intermediate of the humeral handle with an articular surface and a first intermediate of the scapular glenoid plate, putting the two first intermediates into the Sinter-HIP furnace, heating to 1400° C. under argon gas protection, placing at a constant pressure of 140 MPa for 1 h, reducing to a normal pressure, cooling to below 200° C. with the furnace, taking them out, and obtaining a second intermediate of the humeral handle and a second intermediate of the scapular glenoid plate;

1-2) Placing two second intermediate products in a programmable thermostat to cool to −120° C. at a rate of 1° C./min, keeping them at a constant temperature for 5 h, and taking them out of the programmed thermostat; placing them in a liquid nitrogen for 36 h, and adjusting the temperature to a room temperature so as to obtain a third intermediate of the humeral handle and a third intermediate of the scapular glenoid plate;

1-3) Placing two third intermediate products in a programmable thermostat to cool to −120° C. at a rate of 1° C./min, and placing them at a constant temperature for 5 h, taking them out of the programmed thermostat, placing them in the liquid nitrogen for 36 h and adjusting the temperature to room temperature so as to obtain a fourth intermediate of the humeral handle and a fourth intermediate of the scapular glenoid plate;

1-4) Machining, finishing, polishing, cleaning, and drying the fourth intermediate products, and obtaining a fifth intermediate of the humeral handle and a fifth intermediate of the scapular glenoid plate; the roughness of the hemispherical groove of the fifth intermediate product of the humeral handle is Ra=0.050 μm;

1-5) Placing the two fifth intermediate products in a tube furnace, introducing normal-pressure argon gas containing 15% of oxygen in percentage by mass, heating to 700° C. at 20° C./min, and cooling down to 495° C. at 0.9° C./min; and cooling to be below 200° C. sequentially, taking them out to obtain the humeral handle with one articular surface and the scapular glenoid plate.

The structure of the humeral handle with an articular surface is the same as its first intermediate, second intermediate, third intermediate, fourth intermediate, and fifth intermediate.

The structure of the scapular glenoid plate is the same as its first intermediate, second intermediate, third intermediate, fourth intermediate, and fifth intermediate.

2) Preparation of Humeral Head 2-1) Machining, finishing, polishing, cleaning, and drying forged pieces containing zirconium-niobium alloy to obtain the intermediate product of the humeral head;

the roughness of the outer surface of the intermediate products of the humeral head is Ra=0.050 μm;

2-2) placing the intermediate product of the humeral head in a tubular furnace, introducing normal-pressure argon gas containing 15% of oxygen in percentage by mass, heating to 700° C. at 20° C./min, and cooling to 495° C. at 0.9° C./min; and natural cooling to be below 200° C. sequentially, taking them out to obtain the humeral head.

The shoulder joint prosthesis containing zirconium-niobium alloy on oxidation layer comprises a humeral handle 1, an articular surface 12, a humeral head 2 and a scapular glenoid plate 3, the upper end of the articular surface 12 is provided with a hemispherical groove 13, the humeral head 2 is connected with the hemispherical groove 13 in a sliding mode, and the humeral head 2 is buckle-connected with the scapular glenoid plate 3; the scapular glenoid plate 3 is fixedly connected with a circular pipe 33 with internal thread and a hole 31 with internal thread, and the humeral handle 1 and the articular surface 12 are fixedly connected into a humeral handle with articular surface; a bone trabeculae 4 is arranged on the outer surface of the upper part of the humeral handle 1, the upper surface of the scapular glenoid plate 3 and the outer surface of the circular pipe 33.

The chemical composition of the zirconium-niobium alloy powder in percentage by mass is respectively 96.5% of Zr, 1.0% of Nb, and the rest are unavoidable impurities; where a particle size of the zirconium-niobium alloy powder ranges from to 150 μm, which is purchased from Xi'an Sailong Metal Material Co., Ltd.

The chemical composition of the forged pieces containing zirconium-niobium alloy powder in percentage by mass is respectively 96.5% of Zr, 1.0% of Nb, and the rest are unavoidable impurities, which is purchased from Xi'an Sailong Metal Material Co., Ltd.

The specific steps for adjusting the temperature in steps 1-2) and 1-3) are: increasing the temperature to −80° C. and keeping the constant temperature for 3 h; then increasing the temperature to −20° C. and keeping the constant temperature for 3 h and then increasing the temperature to 8° C. and keeping the constant temperature for 1 h and then increasing the temperature.

The pore size of the bone trabeculae 4 is 1.10 mm, the porosity is 78%, through-hole ratio is 100%.

Control Group 1

Using zirconium-niobium alloy powder as Embodiment 1 as a raw material, conducting a 3D printing for one-piece molding, and obtaining a humeral handle with one articular surface and a scapular glenoid plate which structure is same as that of the Embodiment 1.

Figure 6:
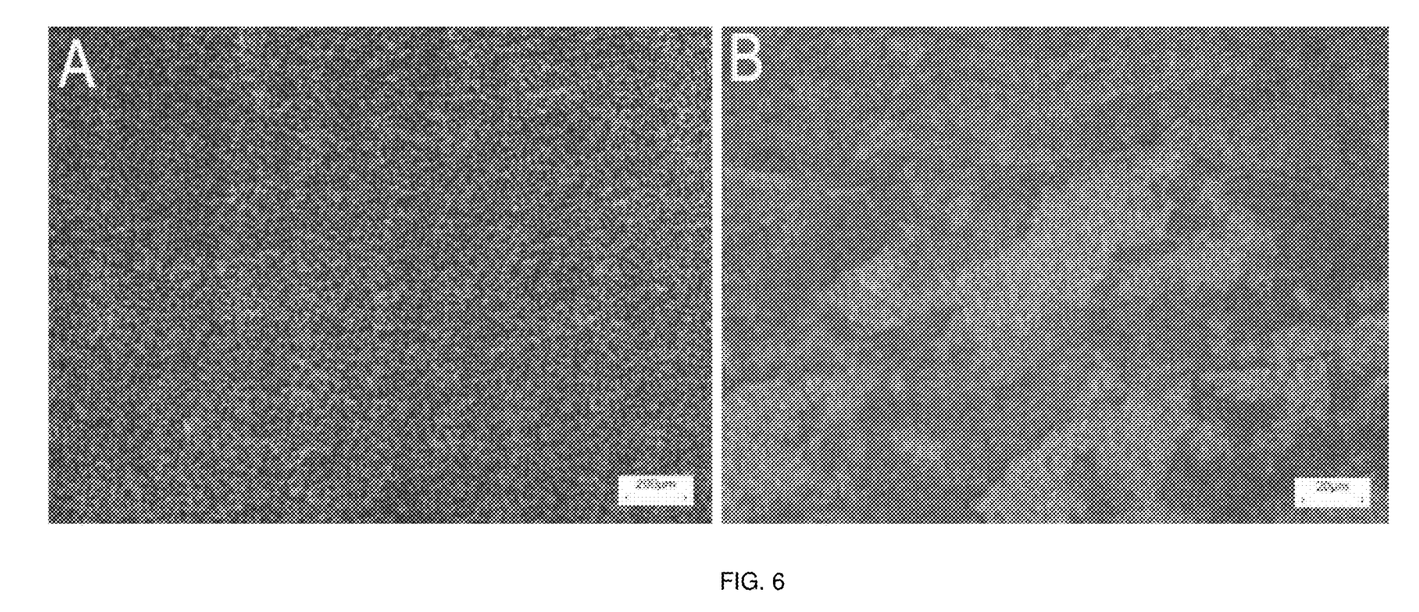
FIG. 6 shows the metallographic micro structure of the solid part of the humeral handle with articular surface in Control Group 1, wherein A is observed by 50 times magnification; B is observed by 500 times magnification.
Figure 7:
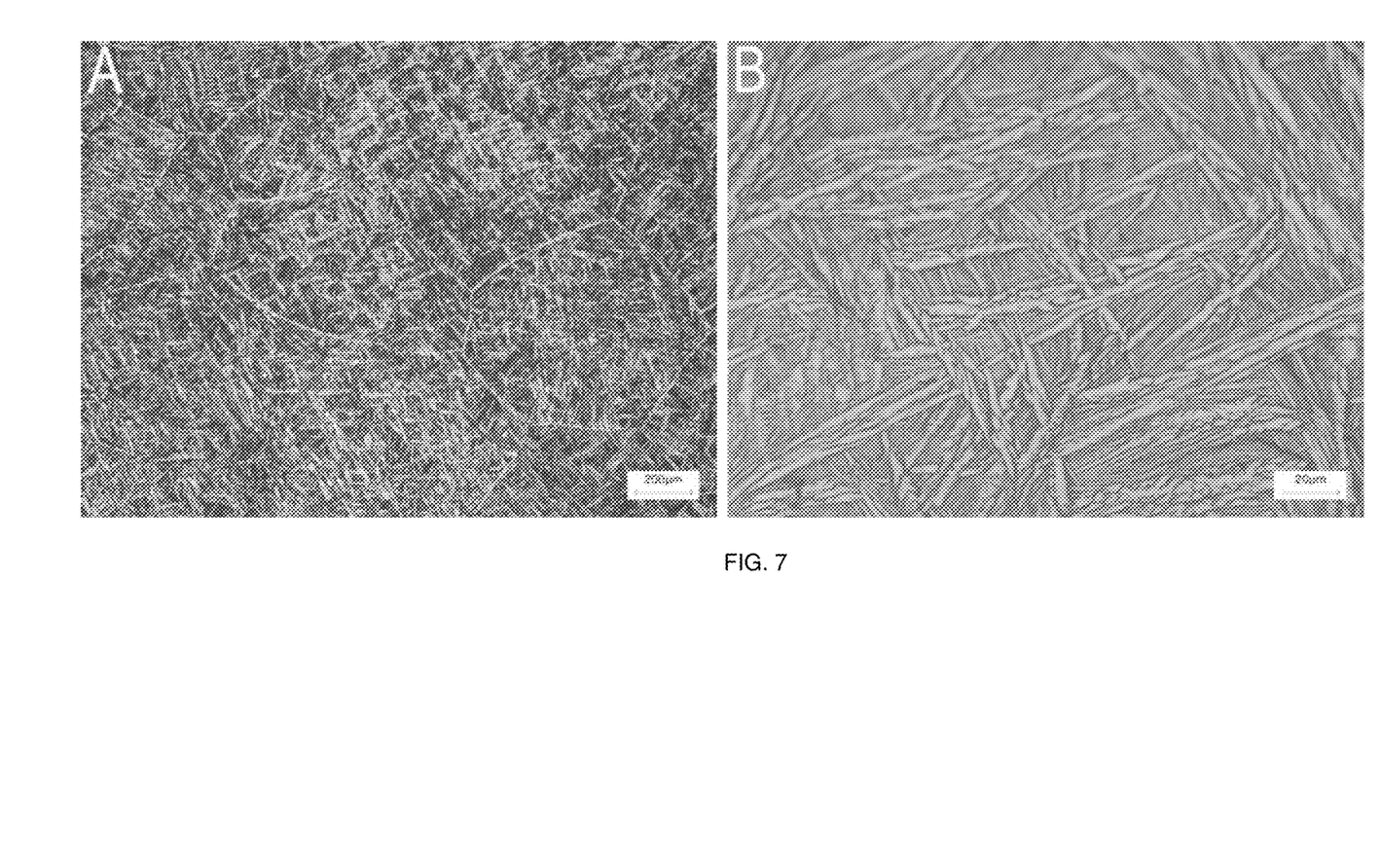
FIG. 7 shows the metallographic microscopic structure of the solid body of the humeral handle with articular surface in Embodiment 1 that has not been prepared with step 1-4) and step 1-5) in the preparation method.

A solid part of the humeral handle with one articular surface in the control group 1 and a humeral handle with one articular surface of the embodiment 1 that has not been prepared with step 1-4) and 1-5) were observed and analyzed by an inverted scanning electron microscope (Axio Vert.A1, Zeiss, Germany). The results were shown in FIGS. 6-7. In the metallographic photos of the humeral handle of the Control Group 1, small a martensite can be observed. The structure is small, easy for stress concentration, and the plasticity is poor. In the metallograph of the humeral handle of the Embodiment 1, a phase can be observed, basket net structure, grain refinement. The results indicated that the solid part (without oxidation layer) of the humeral handle of the shoulder joint prosthesis of the present disclosure has excellent strength and plasticity.

Figure 8:
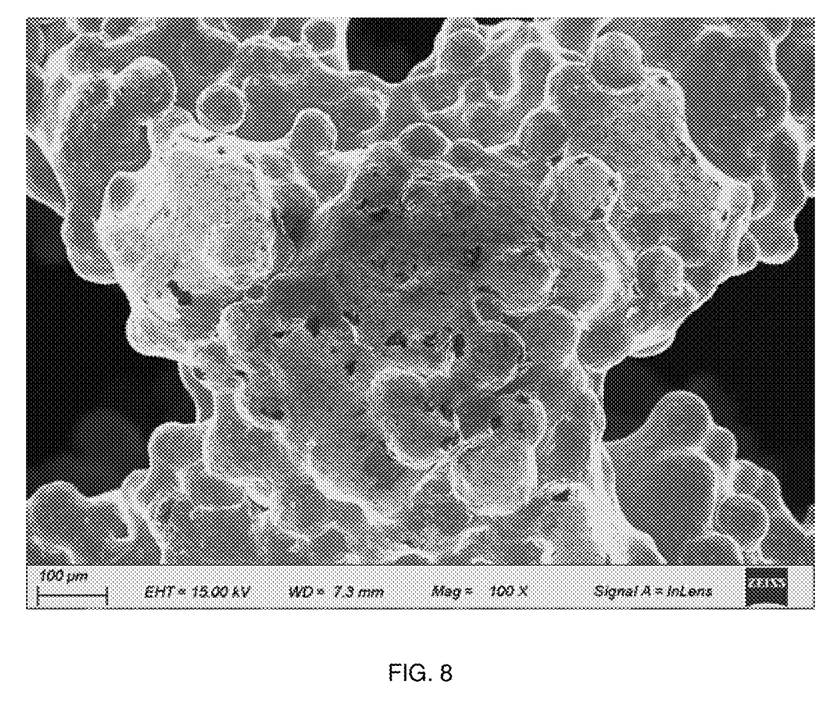
FIG. 8 shows the SEM of bone trabeculae of the humeral handle of Control Group 1.
Figure 9:
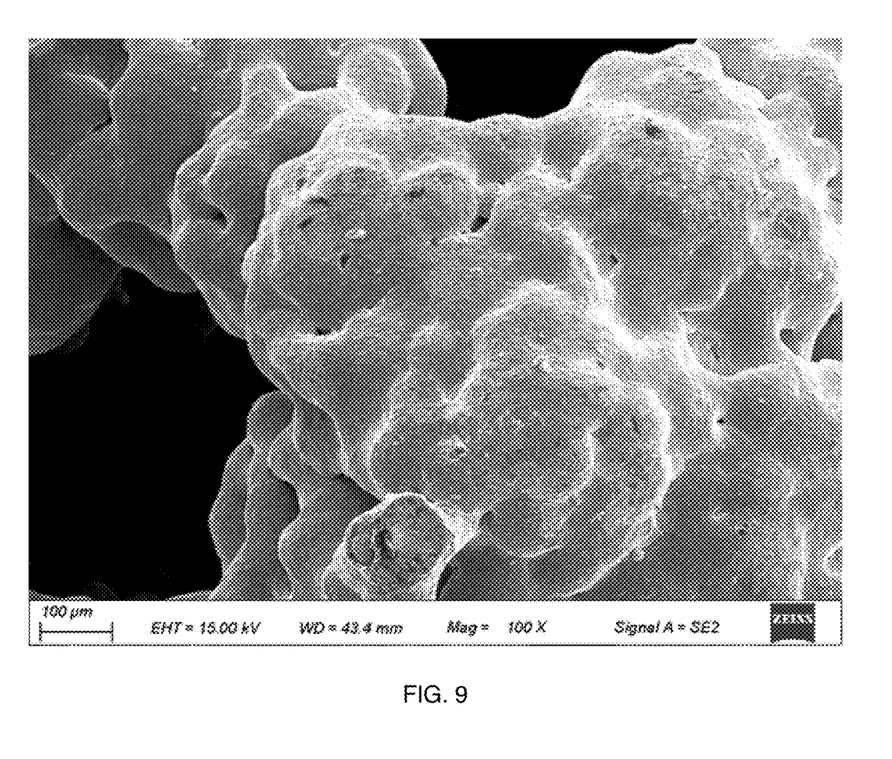
FIG. 9 shows the SEM of bone trabeculae of the humeral handle in Embodiment 1 that has not been prepared with step 1-4) and step 1-5) in the preparation method.

The bone trabeculae of the humeral handle in the control group 1 and the bone trabeculae of the humeral handle of the embodiment 1 that has not been prepared with step 1-4) and 1-5) were observed and analyzed by scanning electron microscopy (Crossbeam340/550, Zeiss, Germany), the results are shown in FIGS. 8-9. Compared with the Control Group 1, the zirconium-niobium alloy powder in the bone trabecula structure of the humeral handle in Embodiment 1 was further sintered, indicating that a combination property of the bone trabeculae was improved.

A physical compression test piece (size: 8*8*10 mm$^3$) of the humeral handle the that has not been prepared with step 1-4) and 1-5) in the preparation method in the embodiment 1 and a physical compression test piece (size: 8*8*10 mm$^3$) of the humeral handle in the control group 1 were subjected to a compression performance test by an electronic universal testing machine (UTM5105, Shenzhen SUNS Technology Co., Ltd., and China). There were 5 physical compression test pieces respectively in the embodiment 1 and the control group 1. Results were shown in Table 1. The compressive yield strength of embodiment 1 is 546.72 MPa, better than that of Control Group 1 (P<0.05), suggesting that the solid part of the humeral handle prepared by the present disclosure has excellent anti-compression performance.

TABLE 1

Anti-compression experiment results of the solid specimens of Control Group 1 and Embodiment 1 ($\bar{x} \pm s$, n = 5, *P < 0.05, compared with Control Group 1)

| Group | Cross-sectional Area (mm$^2$) | Yield Load (kN) | Yield Strength (MPa) |
|---|---|---|---|
| Embodiment 1 | 64 | 34.99 ± 4.04* | 546.72 ± 63.19* |
| Control Group 1 | 64 | 23.59 ± 2.30 | 368.63 ± 35.92 |

A bone trabecula compression specimens with pore size of 0.80 mm, porosity of 72% and through-hole rate of 100% of the humeral handle of the Control Group 1 and the bone trabecula compression specimens with pore size of 0.80 mm, porosity of 72% and through-hole rate of 100% of the humeral handle of Embodiment 1 (specimen size: 8*8*10 mm$^3$) that has not been prepared with step 1-4) and step 1-5) of the above-mentioned preparation method, were subjected to a compression test by the electronic universal testing machine (UTM5105, Shenzhen SUNS Technology Co., Ltd., and China). Bone trabecula compression specimens of the Control Group 1 and the Embodiment 1 were 5 pieces each. The results are shown in Table 2. The compressive yield strength of Embodiment 1 is 18.39 MPa, significantly better than that of Control Group 1 (P<0.05), suggesting that the bone trabecular part of the humeral handle prepared by the present disclosure has excellent anti-compression performance.

TABLE 2

Anti-compression experiment results of the bone trabecular specimens of Control Group 1 and Embodiment 1 ($\bar{x} \pm s$, n = 5, *P < 0.05, compared with Control Group 1)

| Group | Cross-sectional Area (mm$^2$) | Yield Load (N) | Yield Strength (MPa) |
| --- | --- | --- | --- |
| Embodiment 1 | 64 | 1177.24 ± 91.66* | 18.39 ± 1.43* |
| Control Group 1 | 64 | 926.12 ± 106.13 | 14.47 ± 1.66 |

Figure 10:
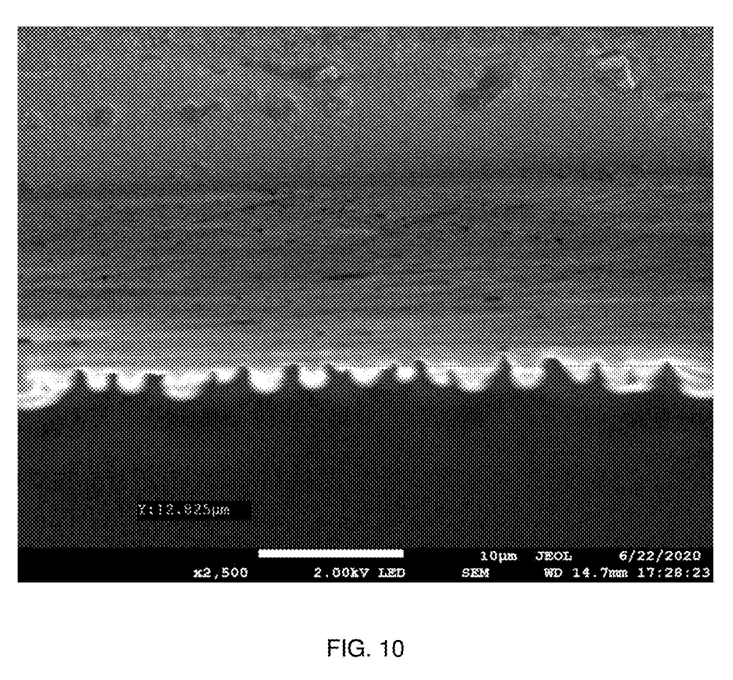
FIG. 10 shows the SEM of cross section of oxidation layer of the humeral handle and matrix in Embodiment 1.

The cross-section of the matrix and oxidation layer of the zirconium-niobium alloy of the humeral handle of the Embodiment 1 was observed by scanning electron microscopy (Crossbeam340/550, Zeiss, Germany) (see FIG. 10). The cross sections of the matrix and oxidation layer of the zirconium-niobium alloy in Embodiments 2 and 3 were observed. The oxidation layer thickness were 10.3 μm, 17.2 μm and 20.6 μm, respectively. There was an oxygen-rich layer between the oxidation layer and the matrix of the zirconium-niobium alloy to enhance the bonding force between the matrix and oxidation layer of zirconium-niobium alloy.

Figure 11:
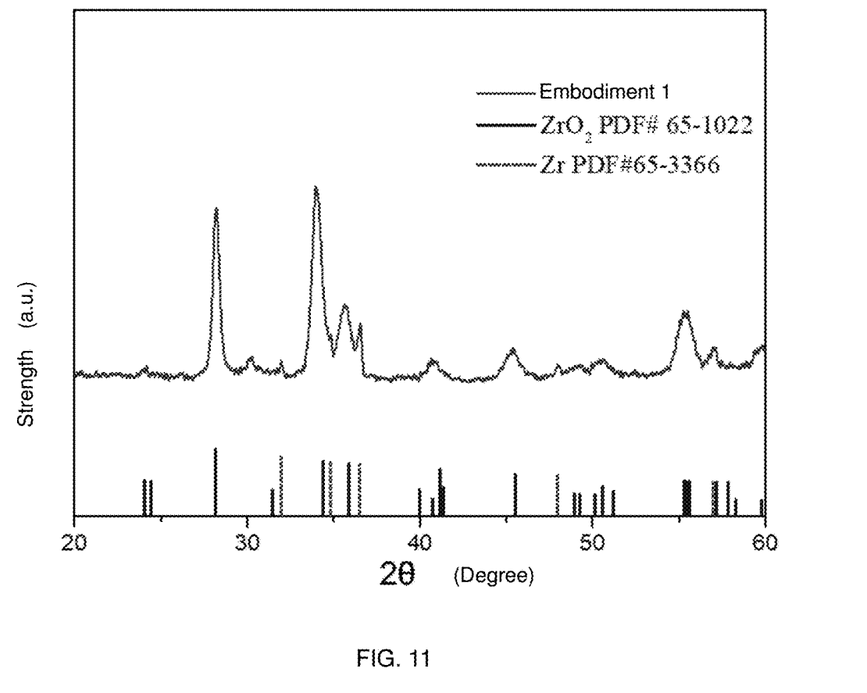
FIG. 11 shows the XRD curve of oxidation layer surface of the humeral handle in Embodiment 1.

XRD (D8DISCOVER, Bruker, Germany) analyzed the oxidation layer of the humeral handle of Embodiment 1 (FIG. 11). The oxidation layer contained monoclinic phase zirconia and tetragonal phase zirconia.

The microhardness measurement on the humeral handle of Embodiments 1-3 was determined by a microhardness tester (MHVS-1000 PLUS, Shanghai Aolongxingdi Testing Equipment Co., Ltd., China), in which the load was 0.05 kg, the load time of the specimens was 20 s, and 8 points were taken for each specimen. The average hardness values measured in Embodiments 1-3 were 1948.6 Hv, 1923.7 Hv, and 1967.2 Hv, suggesting that the oxidation layer in the humeral handle of the present disclosure has high hardness.

Experiments have proved that the zirconium-niobium alloy powder bonding degree, compressive properties, compressive properties and metallographic structure of the solid part, the crystal structure of the oxidation layer, thickness and hardness of the oxidation layer for the humeral handle with articular surface and the scapular glenoid plate prepared in Embodiments 2 and 3 are similar to that of the humeral handle with articular surface prepared in Embodiment 1. The crystal structure, thickness and hardness of the oxidation layer of the humeral head prepared in Embodiments 1, 2 and 3 are similar to that of the humeral handle with articular surface prepared in Embodiment 1.

The invention claimed is:

1. A preparation method of a shoulder joint prosthesis containing zirconium-niobium alloy on oxidation layer comprising the following steps:

1) Preparation of humeral handle with one articular surface or scapular glenoid plate 1-1) using zirconium-niobium alloy powder as the raw material, conducting a 3D printing for one-piece molding, and obtaining a first intermediate of the humeral handle with an articular surface and a first intermediate of the scapular glenoid plate, putting the two first intermediates into the Sinter-HIP furnace, heating to 1250° C.-1400° C. under helium/argon gas protection, placing at a constant pressure of 140 MPa-180 MPa for 1h to 3h, reducing to a normal pressure, cooling to below 200° C. with the furnace, taking them out, and obtaining a second intermediate of the humeral handle and a second intermediate of the scapular glenoid plate;

1-2) placing the second intermediate of the humeral handle and the second intermediate of the scapular glenoid plate in a programmable thermostat to cool to −80° C. to −120° C. at a rate of 1° C./min, keeping them at a constant temperature for 5 h to 10 h, and taking them out of the programmed thermostat; placing them in a liquid nitrogen for 16 h to 36 h, and adjusting the temperature to a room temperature so as to obtain a third intermediate of the humeral handle and a third intermediate of the scapular glenoid plate;

1-3) placing the third intermediate of the humeral handle and the third intermediate of the scapular glenoid plate in a programmable thermostat to cool to −80° C. to −120° C. at a rate of 1° C./min, and placing them at a constant temperature for 5 h to 10 h, taking them out of the programmed thermostat, placing them in the liquid nitrogen for 16 h to 36 h and adjusting the temperature to room temperature so as to obtain a fourth intermediate of the humeral handle and a fourth intermediate of the scapular glenoid plate;

1-4) machining, finishing, polishing, cleaning, and drying the fourth intermediate products, and obtaining a fifth intermediate of the humeral handle and a fifth intermediate of the scapular glenoid plate; the roughness of the hemispherical groove of the fifth intermediate product of the humeral handle is Ra≤0.050 μm;

1-5) placing the two fifth intermediate products in a tube furnace, introducing normal-pressure helium/argon gas containing 5% to 15% of oxygen in percentage by mass, heating to 500° C. to 700° C. at 5° C./min to 20° C./min, and cooling down to 400° C. to 495° C. at 0.4° C./min to 0.9° C./min; and cooling to be below 200° C. sequentially, taking them out to obtain the humeral handle with one articular surface and the scapular glenoid plate;

the structure of the humeral handle with the articular surface is the same as its first intermediate, second intermediate, third intermediate, fourth intermediate, and fifth intermediate;

the structure of the scapular glenoid plate is the same as its first intermediate, second intermediate, third intermediate, fourth intermediate, and fifth intermediate;

2) Preparation of humeral head 2-1) machining, finishing, polishing, cleaning, and drying forged pieces containing zirconium-niobium alloy to obtain the intermediate product of the humeral head; the roughness of the outer surface of the intermediate products of the humeral head is Ra≤0.050 μm;

2-2) placing the intermediate product of the humeral head in a tubular furnace, introducing normal-pressure helium/argon gas containing 5% to 15% of oxygen in percentage by mass, heating to 500° C. to 700° C. at 5° C./min to 20° C./min, and cooling to 400° cto 495° C. at 0.4° C./min to 0.9° C./min; and natural cooling to be below 200° C. sequentially, taking them out to obtain the humeral head;

the shoulder joint prosthesis containing zirconium-niobium alloy on oxidation layer comprises the humeral handle (1), the articular surface (12), the humeral head 2 and a scapular glenoid plate (3), the upper end of the articular surface (12) is provided with a hemispherical groove (13), the humeral head (2) is connected with the hemispherical groove (13) in a sliding mode, and the humeral head (2) is buckle-connected with the scapular glenoid plate (3); the scapular glenoid plate (3) is fixedly connected with a circular pipe (33) with internal thread and a hole (31) with internal thread, and the humeral handle (1) and the articular surface (12) are fixedly connected into the humeral handle with the articular surface; a bone trabeculae (4) is arranged on the outer surface of the upper part of the humeral handle (1), the upper surface of the scapular glenoid plate (3) and the outer surface of the circular pipe (33).

2. The preparation method according to claim 1, wherein the chemical composition of the zirconium-niobium alloy powder in percentage by mass is respectively 85.6%-96.5% of Zr, 1.0%-12.5% of Nb, and the rest are unavoidable impurities;

where a particle size of the zirconium-niobium alloy powder ranges from 45 to150 μm.

3. The preparation method according to claim 1, wherein the chemical composition of the forged pieces containing zirconium-niobium alloy powder in percentage by mass is respectively 85.6%-96.5% of Zr, 1.0%-12.5% of Nb, and the rest are unavoidable impurities.

4. The preparation method according to claim 1, wherein the specific steps for adjusting the temperature in steps 1-2) and 1-3) are: increasing the temperature to −120° C. to −80° C. and keeping the constant temperature for 3h to 5 h; then increasing the temperature to −40° C. to −20° C. and keeping the constant temperature for 3h to 5 h and then increasing the temperature to 4° C. to 8° C. and keeping the constant temperature for 1h to 3 h and then increasing the temperature.

5. The preparation method according to claim 1, wherein the pore size of the bone trabeculae (4) ranges from 0.35 mm to 1.10 mm, the porosity ranges from 55% to 78%, through-hole ratio is 100%.

6. The shoulder joint prosthesis containing zirconium-niobium alloy on oxidation layer prepared by the preparation method according claim 1.

7. The shoulder joint prosthesis containing zirconium-niobium alloy on oxidation layer prepared by the preparation method according claim 2.

8. The shoulder joint prosthesis containing zirconium-niobium alloy on oxidation layer prepared by the preparation method according claim 3.

9. The shoulder joint prosthesis containing zirconium-niobium alloy on oxidation layer prepared by the preparation method according claim 4.

10. The shoulder joint prosthesis containing zirconium-niobium alloy on oxidation layer prepared by the preparation method according claim 5.

* * * * *